United States Patent [19]
Lee et al.

[11] Patent Number: 6,093,814
[45] Date of Patent: Jul. 25, 2000

[54] PROCESS FOR PREPARATION OF CEFDINIR

[75] Inventors: Gwan Sun Lee; Young Kil Chang, both of Seoul; Jong Pil Chun, Daejeon; Joon Hyung Koh, Kwacheon-shi, all of Rep. of Korea

[73] Assignee: Hanmi Pharmaceutical Co., Ltd., Kyunggi-do, Rep. of Korea

[21] Appl. No.: 09/068,719

[22] PCT Filed: Dec. 26, 1996

[86] PCT No.: PCT/KR96/00250

§ 371 Date: May 18, 1998

§ 102(e) Date: May 18, 1998

[87] PCT Pub. No.: WO97/24358

PCT Pub. Date: Jul. 10, 1997

[30] Foreign Application Priority Data

Dec. 27, 1995 [KR] Rep. of Korea ............... 95-58694
Dec. 27, 1995 [KR] Rep. of Korea ............... 95-58695

[51] Int. Cl.$^7$ .................. C07D 501/04; C07D 501/22
[52] U.S. Cl. .................................................. 540/222
[58] Field of Search ........................................... 540/222

[56] References Cited

FOREIGN PATENT DOCUMENTS

95/35 020 A2  12/1995  WIPO .

OTHER PUBLICATIONS

Tsuji, Tet. Letters, pp. 2793–2796, 1979.

Chemical Abstracts, vol. 114, No. 7, Feb. 18, 1991 (Columbus, Ohio, USA), p. 656 Col. 1, abstract No. 61761t, Sakane K. et al.: "Studies on FK482 (Cefdinir). III. Synthesis and structure–activity relationships of 7B–[(Z)–2–aryl–2–hydroxyimio=acetamido]–3–vinyl–3–vinyl–3–cephem–4–carboxylic acid derivatives", & Yakagaku Zasshi 1990, 110(9), 658–64 (Japan).

Chemical Abstracts, vol. 114, No. 15, Apr. 15, 1991 (columbus, Ohio, USA), p. 734, col. 1, abstract No. 142931a, Inamoto Y. et al.: "Studies on FK482 (Cefdinir). IV. Synthesis and structure–activity relationships of 7B–[(Z)–2–(2–aminothiazol–4–yl)–2–=hydroxyiminacetamido]– 3–substitute cephalosporin derivatives", and Yakagaku Zasshi 1990, 110(12), 908–15 (Japan).

*Primary Examiner*—Mark L. Berch
*Attorney, Agent, or Firm*—McDermott, Will & Emery

[57] ABSTRACT

The present invention relates to a novel crystalline cefdinir intermediate having formula (II) which can be used very usefully for preparing a cephalosporin antibiotics, cefdinir, in which Ph represents phenyl, p-TsOH represents p-toluenesulfonic acid, and DMAC represents N,N-dimethylacetamide, to a process for preparation thereof and to a process for preparing cefdinir using the compound of formula (II).

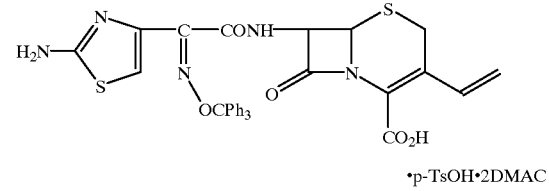

·p-TsOH·2DMAC

According to the present invention, cefdinir can be prepared in an excellent color and purity and with a good yield.

17 Claims, No Drawings

PROCESS FOR PREPARATION OF CEFDINIR

This application is the national phase of [claims priority under 35 U.S.C. § 371 to] PCT Application No. PCT/KR96/00250 [100250], filed Dec. 26, 1996.

TECHNICAL FIELD

The present invention relates to a process for preparing cefdinir represented by the following formula (I) as a cephalosporin antibiotics:

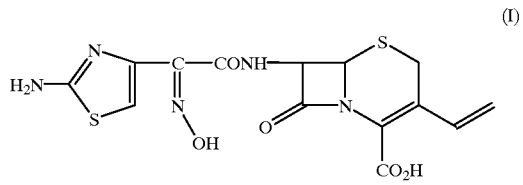

BACKGROUND ART

Cefdinir of formula (I) above has a chemical name of 7β-[2-(2-aminothiazol-4-yl)-2-(Z)-(hydroxyimino) acetamido]-3-vinyl-3-cep-hem-4-carboxylic acid. It is the third generation of cephalosporin antibiotics for oral administration and has a broader antibacterial spectrum over the general gram positive and gram negative bacteria than other antibiotics for oral administration. Particularly, it has been reported that cefdinir has an excellent antibacterial activity against Staphylococci and Streptococci.

In U.S. Pat. No. 4,559,334 is disclosed a process for preparing cefdinir as represented in the following reaction scheme 1.

In the above reaction, 7-amino-3-vinyl-3-cephem-4-carboxylic acid ester(A) is reacted with a reactive carboxylic acid derivative to obtain an 7-amido compound(B), and this compound is treated with a nitrosating agent to prepare an N-oxime compound(C). Continually, the compound(C) is cyclized with thiourea to prepare an aminothiazol compound (D), and then finally cefdinir of formula (I) is prepared by removing the carboxy protecting group.

In case cefdinir is prepared according to the reaction scheme 1, however, there can occur many problems such that the process for preparing the 7-amido compound(B) should be carried out at a temperature below −20° C. under an anhydrous condition and that the isolation of the N-oxime compound(C) may cause a lot of troubles in the procedure of industrialization since the compound(C) is obtained as a solid having a syrup or a foam phase after the solvent is distilled off under reduced pressure. In addition, the aminothiazole compound(D) is obtained in a poor yield and purity and with a brownish poor color, which finally exerts a harmful influence upon the purity and color of the desired cefdinir. Further, in the reaction scheme 1, since cefdinir is synthesized through a complicated reaction consisting of 4 steps from the expensive 7-amino-3-vinyl-3-cephem-4-carboxylic acid derivative, the cost for production of cefdinir increases according as the whole reaction yield decreases.

DISCLOSURE OF INVENTION

Thus, the present inventors have extensively studied to develop a novel process by which cefdinir can conveniently be prepared in a good yield and a high purity. As a result, we have identified that such a purpose can be achieved by using a novel cefdinir intermediate represented by the following formula (II) as a starting substance and then completed the present invention.

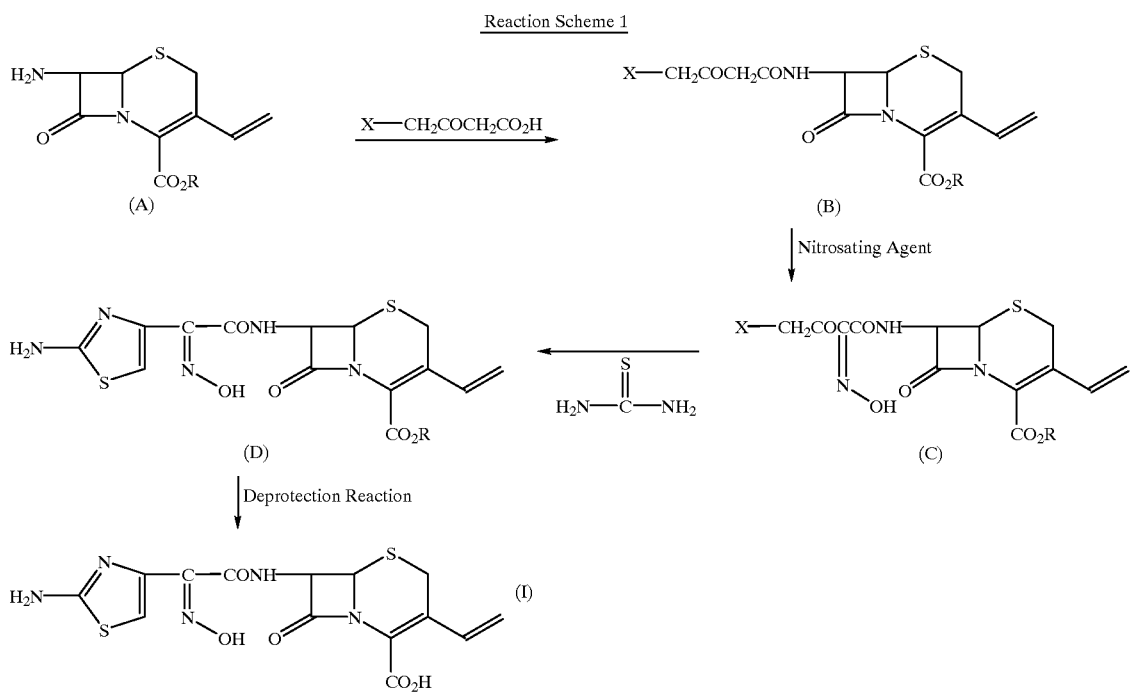

Reaction Scheme 1

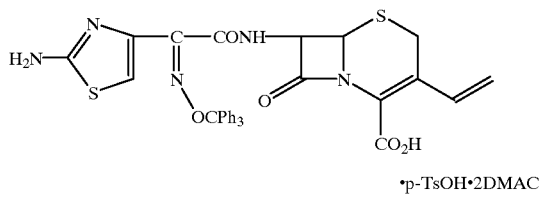

*p-TsOH·2DMAC
(II)

in which
Ph represents phenyl,
p-TsOH represents p-toluenesulfonic acid, and
DMAC represents N,N-dimethylacetamide.

Thus, it is an object of the present invention to provide a novel process for preparing cefdinir using the intermediate of formula (II) as a starting substance.

It is another object of the present invention to provide a novel intermediate of formula (II), as defined above, and process for preparation thereof.

BEST MODE FOR CARRYING OUT THE INVENTION

In one aspect, the present invention pertains to a process for preparing cefdinir of formula (I) characterized in that a trityl protecting group in the cefdinir intermediate of formula (II) is removed in the presence of an acid. The process is depicted in the following reaction scheme 2.

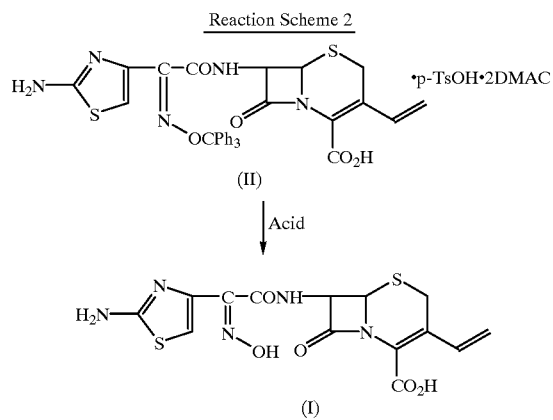

The most important feature in the process for preparing cefdinir according to the present invention is that the novel cefdinir intermediate of formula (II) which is very excellent in yield and purity is used as a starting material.

As the acid which can be used in the process for preparing cefdinir according to the present invention, an inorganic acid such as hydrochloric acid, hydrobromic acid, hydroiodic acid, sulfuric acid, Lewis acid, etc.; an organic acid such as acetic acid, formic acid, trifluoroacetic acid, methanesulfonic acid, benzenesulfonic acid, p-toluenesulfonic acid, etc.; or an acidic hydrogen ion exchange resin can be mentioned, wherein Lewis acid includes boron trifluoride, boron trifluoride ethyletherate, aluminum chloride, antimony pentachloride, ferrous chloride, stannous chloride, titanium tetrachloride, zinc chloride, etc. When an organic acid such as trifluoroacetic acid or p-toluenesulfonic acid, or a Lewis acid is selected, it is preferable that the reaction is carried out in the presence of an anisole as a cation scavenger. The acid is preferably used in an amount of 1 to 20 equivalents with respect to the starting material It is preferable to carry out the reaction at a low temperature in a range of −30 to 5° C. But, the reaction can also be performed at 40 to 70° C. in case of using the acid in an amount of 1 to 2 equivalents with respect to the cefdinir intermediate of formula (II).

As the solvent, one or more selected from a group consisting of water, ethanol, methanol, propanol, t-butanol, tetrahydrofuran, dioxane, N,N-dimethylformamide, N,N-dimethylacetamide, methylene chloride and chloroform can be used, and if desired, the organic acid or inorganic acid itself can be used as a reaction solvent.

The cefdinir of formula (I) prepared according to the process as explained above exhibits a superior quality in color, yield and purity to that prepared according to the earlier process, and such a result is basically caused by use of the cefdinir intermediate of formula (II) as a starting material. That is, this intermediate is a crystalline compound having a pale yellow color and a high purity more than 98%, therefore it's good quality has a beneficial effect on the next step for finally producing cefdinir having an excellent quality.

Generally, the earlier process for preparing cefdinir from the reactive derivative has problems that 1-hydroxybenzotriazole or 2-mercaptobenzothiazole produced during the reaction can hardly be removed from the reaction mixture, which lowers the purity of the reaction product and also makes the purifying step difficult. Upon considering this, the present invention having no such problems can be estimated as an astounding one.

Furthermore, in the prior art, cefdinir can be prepared from the expensive compound(A) through a 4-step reaction. In contrast, in the present invention, only 2 steps of reaction are needed for the preparation of the final product, cefdinir. Therefore, a lot of beneficial effects can be expected by applying the present invention for preparing cefdinir such that a decrease of the yield due to the multi-step reaction can be prevented; the product can be provided with a low price since there is no need to use the expensive material; and the manufacturing time, can be saved by cutting the reaction steps in half, and the like.

In another aspect, the present invention pertains to the compound of formula (II) above and process for preparing the same.

The cefdinir intermediate of formula (II) used as a starting material in the reaction scheme 2 is a crystalline complex with a salt and a solvent, and it can easily be prepared by reacting a reactive ester having the following formula (III) with a 3-cephem derivative having the following formula (IV) in a solvent in the presence or absence of a base and then by adding p-toluenesulfonic acid thereto. The reaction is depicted in the following reaction scheme 3:

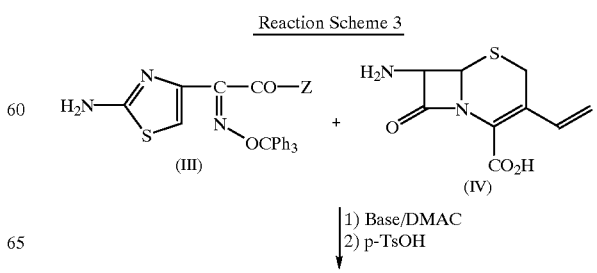

-continued

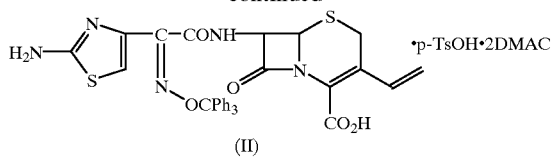

in which

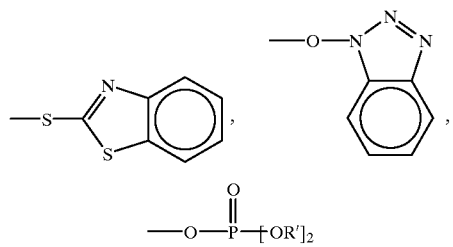

Z represents

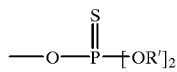

wherein R' represents $C_1$–$C_4$ alkyl or phenyl, or R' together with phosphorus and oxygen atoms to which R' is attached can form a 5 to 6-membered heterocycle.

The reactive ester compound of formula (III) used as a starting substance in the reaction scheme 3 above is a known compound and can be prepared according to the process disclosed in literatures (see, European Patent Laid-open Publication No. 555,769; Japanese Patent Laid-open Publication No. sho 57-175,196). The 3-cephem derivative of formula (IV) can also be prepared easily according to the known method described in U.S. Pat. No. 4,423,213.

The reactive ester compound of formula (III) is used in an amount of 0.8 to 2.0 equivalents, preferably 1.0 to 1.2 equivalents with respect to the 3-cephem derivative of formula (IV). The solvent which can be used in the reaction of scheme 3 includes, N,N-dimethylacetamide alone, or a mixture of N,N-dimethylacetamide with one or more selected from a group consisting of ethanol, methanol, isopropanol, diethylether, tetrahydrofuran, dioxane, methylene chloride, chloroform, acetonitrile, ethyl acetate and acetone. In this case, the solvent is used in an amount of 10 to 60 ml, preferably 10 to 30 ml with respect to 1 g of the 3-cephem derivative of formula (IV).

Generally, the reaction is carried out at a temperature of −15 to 40° C., preferably 0 to 30° C. The reaction is completed after 1 to 24 hours have passed from the initial point, however, it is desirable to complete the reaction within 1 to 5 hours since the color of the reaction solution becomes poor and the amount of side products increases as the reaction time becomes longer.

The process for preparing the compound (II) of the present invention can be carried out in the presence of a base. If a base is used, tertiary amines such as triethylamine, tri-n-butylamine, diisopropylethylamine, triethylenediamine, pyridine, N,N-dimethylaniline, etc., preferably triethylamine or tri-n-butylamine can be used as the base. The base can be used in an amount of 0.5 to 5 equivalents, preferably 1 to 2 equivalents with respect to the 3-cephem derivative of formula (IV). On the other hand, the reaction can also be carried out by using N-trimethylsilylacetamide or N,O-bistrimethylsilylacetamide in an amount of 1 to 3 equivalents with respect to the 3-cephem derivative of formula (IV) instead of the base.

After the reaction is completed under the conditions as explained above, diethylether, diisopropylether or ethylacetate is added to the reaction mixture to crystallize the product in the work-up procedure. In this case, they are added in an amount of 2 to 6 times by volume with respect to the reaction solvent, however, it is desirable to add them in an amount of 3 to 5 times by volume considering the reaction yield and purity.

On the other hand, p-toluenesulfonic acid is usually used in an amount of 1 to 4 equivalents, preferably 2 to 3 equivalents with respect to the 3-cephem derivative of formula (IV).

The cefdinir intermediate of formula (II) thus produced is a crystalline complex with a salt and a solvent, and it has a unique structure wherein one molecule of p-toluenesulfonic acid and two molecules of N,N-dimethylacetamide are attached to the main structure. Accordingly, it can be isolated more easily from the reaction mixture in a high purity than the usual cephalosporin compound having a noncrystalline form.

It is recognized through a X-ray powder diffraction analysis that the compound (II) has a different crystalline form from other noncrystalline compounds. Particularly, in the X-ray powder diffraction spectrum of FIG. 1, the characteristic peak; of the compound (II) is well represented. The unique Debye-Scherrer X-ray powder diffraction pattern of the crystalline compound of formula (II) is described in the following Table 1.

In Table 1 below, "θ" represents a diffraction angle, "d" represents a spacing between the layers, and "$I/I_o$" represents a relative intensity.

TABLE 1

Debye-Scherrer X-ray powder diffraction pattern of the compound of formula (II)

| θ | d | I / Io | θ | d | I / Io |
|---|---|---|---|---|---|
| 4.28 | 20.63 | 18 | 19.64 | 4.52 | 19 |
| 8.06 | 10.96 | 29 | 20.32 | 4.37 | 20 |
| 8.36 | 10.57 | 38 | 20.62 | 4.31 | 51 |
| 8.88 | 9.95 | 22 | 20.82 | 4.26 | 28 |
| 9.14 | 9.67 | 18 | 21.06 | 4.21 | 46 |
| 10.08 | 8.77 | 15 | 21.58 | 4.11 | 34 |
| 11.22 | 7.88 | 34 | 21.76 | 4.08 | 23 |
| 11.44 | 7.73 | 28 | 22.24 | 3.99 | 20 |
| 12.02 | 7.36 | 33 | 22.58 | 3.93 | 18 |
| 12.92 | 6.85 | 20 | 23.02 | 3.86 | 25 |
| 13.28 | 6.66 | 32 | 23.34 | 3.81 | 17 |
| 15.24 | 5.81 | 18 | 23.48 | 3.79 | 21 |
| 15.56 | 5.69 | 27 | 24.24 | 3.67 | 39 |
| 16.20 | 5.47 | 22 | 25.04 | 3.55 | 21 |
| 16.76 | 5.29 | 19 | 25.12 | 3.54 | 16 |
| 17.14 | 5.17 | 95 | 25.70 | 3.46 | 29 |
| 17.24 | 5.14 | 81 | 26.04 | 3.42 | 19 |
| 17.62 | 5.03 | 29 | 26.62 | 3.35 | 16 |
| 18.14 | 4.89 | 69 | 27.22 | 3.27 | 17 |
| 18.50 | 4.79 | 87 | 27.76 | 3.21 | 16 |
| 18.54 | 4.78 | 100 | 29.28 | 3.05 | 18 |
| 18.76 | 4.73 | 60 | 29.48 | 3.03 | 20 |

In addition, the structure of the intermediate (II) is identified qualitatively through IR and NMR spectroscopy (see, FIG. 1 to 3)

Hereinafter, the present invention will be more specifically explained by the following examples. However, it should be understood that the following examples are intended to illustrate the present invention and not to limit the scope of the present invention in any manner.

EXAMPLE 1

Synthesis of 7β-[2-(2-aminothiazol-4-yl)-2(Z)-(trityloxyimino)acetamido]-3-vinyl-3-cephem-4-carboxylic acid•p-toluene sulfonic acid•2 N,N-dimethylacetamide 8.0 g (35.4 mmol) of 7-amino-3-vinyl-3-cephem-4-carboxylic acid and 21.5 g (37.1 mmol) of (Z)-(2-aminothiazol-4-yl)-2-trityloxyiminoacetic acid 2-benzothiazolyl thioester were suspended in 80 ml of N,N-dimethylacetamide and 16.8 ml (70.0 mmol) of tri-n-butylamine was added thereto. Then, the reaction mixture was stirred for 1 hour while keeping the temperature at 15 to 20° C. and 240 ml of diethylether was added to the mixture. The reaction mixture thus prepared was stirred for 30 minutes and then filtered through a cellite. To the filtrate was added 20.2 g (0.11 mol) of p-toluenesulfonic acid•monohydrate dissolved in 40 ml of methanol and the resulting solution was stirred for 2 hours at room temperature. After 160 ml of diethylether was further added thereto, the whole solution was stirred for one hour at room temperature, cooled to 0 to 5° C., stirred for one hour and filtered. The crystal thus obtained was washed sequentially with 50 ml of N,N-dimethylacetamide-diethylether(1:5, v/v) and 50 ml of diethylether and then dried to obtain 32.3 g (Yield 93%) of the title compound as a pale yellow crystal.

HPLC Purity: 99.2%;
m.p.(°C.): 164–165;
IR(KBr, cm$^{-1}$): 3061, 1780, 1622, 1192;
$^1$H-NMR(MeOH-d$_4$)δ: 2.0(s,6H), 2.3(s,3H), 2.9(s,6H), 3.0(s,6H), 3.7(s,2H), 5.0–6.0(m,4H), 6.9–7.5(m,17H), 7.7 (d,2H,J=8 Hz).

EXAMPLE 2

10.0 g (44.0 mmol) of 7-amino-3-vinyl-3-cephem-4-carboxylic acid and 27.0 g (46.4 mmol) of (Z)-(2-aminothiazol-4-yl)-2-trityloxyiminoacetic acid 2-benzothiazolylthioester were mixed in 200 ml of N,N-dimethylacetamide. 22.0 ml (89.0 mmol) of N,O-bistrimethylsilylacetamide was added thereto and then the resulting mixture was stirred overnight at 10 to 20° C. After 600 ml of diethylether and 10 ml of methanol were added to the mixture, the whole mixture was stirred for 30 minutes and then filtered through a cellite. To the filtrate was added 12.6 g (66.2 mmol) of p-toluenesulfonic acid•monohydrate dissolved in 40 ml of methanol and the resulting solution was stirred for 3 hours. After 400 ml of diethylether was further added thereto, the solution was stirred for 2 hours and then filtered. The crystal thus obtained was washed sequentially with 60 ml of N,N-dimethylacetamide-diethylether(1:5, v/v) and 100 ml of diethylether and then dried to obtain 38.3 g (Yield 88%) of 7β-[2-(2-(2-aminothiazol-4-yl)-2(Z)-(trityloxyimino)acetamido]-3-vinyl-3-cephem-4-carboxylic acid•p-toluenesulfonic acid•2 N,N-dimethylacetamide as a pale yellow crystal. The purity of the product determined by HPLC analysis was 99.4%, and melting point, IR and $^1$H-NMR data were identical to those described in Example 1.

EXAMPLE 3

18.9 g (32.5 mmol) of diethylthiophosphoryl (Z)-(2-aminothiazol-4-yl)-2-trityloxyiminoacetate was dissolved in 105 ml of N,N-dimethyl acetamide. 7.0 g (31 mmol) of 7-amino-3-vinyl-3-cephem-4-carboxylic acid and 8.6 ml (62 mmol) of triethylamine were added thereto and then the resulting mixture was stirred for 2 hours at room temperature. 210 ml of diethylether was added to the mixture, which was then stirred for 30 minutes and filtered through a cellite. To the filtrate was added 17.7 g (93 mmol) of p-toluenesulfonic acid•monohydrate dissolved in 25 ml of ethanol and the resulting solution was stirred for one hour and a half. After 210 ml of diethylether was further added thereto, the solution was filtered to obtain a crystal. The crystal thus obtained was washed sequentially with 50 ml of N,N-dimethylacetamide-diethylether(1:5, v/v) and 50 ml of diethylether and then dried to obtain 26.2 g (Yield 86%) of 7β-[2-(2-aminothiazol-4-yl)-2(Z)-(trityloxyimino) acetamido]-3-vinyl-3-cephem-4-carboxylic acid•p-toluenesulfonic acid•2 N,N-dimethylacetamide as a pale yellow crystal. The purity of the product determined by HPLC analysis was 98.5%, and melting point, IR and $^1$H-NMR data were identical to those described in Example 1.

EXAMPLE 4

10.0 g (44.0 mmol) of 7-amino-3-vinyl-3-cephem-4-carboxylic acid and 27.0 g (46.4 mmol) of (Z)-(2-aminothiazol-4-yl)-2-trityloxyiminoacetic acid 2-benzothiazolylthioester were suspended in 150 ml of N,N-dimethylacetamide. 21.0 ml (88.0 mmol) of tri-n-butylamine was added thereto and the mixture was stirred for 1 hour and a half at 15 to 25° C. 25.2 g (133 mmol) of p-toluenesulfonic acid•monohydrate was added to the mixture and thoroughly dissolved, 450 ml of diisopropylether was added thereto and then the whole mixture was stirred for 2 hours. After 300 ml of diisopropylether was added to the mixture, the resulting solution was stirred for 2 hours, cooled to about 5° C., stirred for 1 hour and filtered to obtain a crystal. The crystal thus obtained was washed sequentially with 50 ml of N,N-dimethylacetamide-diethylether(1:5, v/v) and 50 ml of diethylether and then dried to obtain 41.8 g (Yield 96%) of 7β-[2-(2-aminothiazol-4-yl)-2(Z)-(trityloxyimino)acetamido]-3-vinyl-3-cephem-4-carboxylic acid•p-toluenesulfonic acid•2 N,N-dimethylacetamide as a pale yellow crystal. The purity of the product determined by HPLC analysis was 98.2%, and melting point, IR and $^1$H-NMR data were identical to those described in Example 1.

EXAMPLE 5

10.0 g (44.0 mmol) of 7-amino-3-vinyl-3-cephem-4-carboxylic acid and 30.8 g (53 mmol) of (Z)-(2-aminothiazol-4-yl)-2-trityloxyiminoacetic acid 2-benzothiazolylthioester were mixed in 200 ml of N,N-dimethylacetamide. 21.1 ml (88 mmol) of tri-n-butylamine was added thereto and then the resulting mixture was stirred overnight at room temperature. After 400 ml of diethylether and 2 g of activated charcoal were added to the mixture, the whole mixture was stirred for 1 hour and then filtered through a cellite. To the filtrate was added 16.8 g (88 mmol) of p-toluenesulfonic acid•monohydrate dissolved in 30 ml of methanol and the resulting solution was stirred for 2 hours. After 400 ml of diethylether was further added thereto, the solution was stirred for 2 hours and then filtered. The crystal thus obtained was washed sequentially with 50 ml of N,N-dimethylacetamide-diethylether(1:5, v/v) and 50 ml of diethylether and then dried to obtain 37.0 g (Yield 85%) of 7β-[2-(2-aminothiazol-4-yl)-2(Z)-(trityloxyimino) acetamido]-3-vinyl-3-cephem-4-carboxylic acid•p-toluenesulfonic acid•2 N,N-dimethylacet-amide as a pale yellow crystal. The purity of the product determined by HPLC analysis was 98.5%, and melting point, IR and $^1$H-NMR data were identical to those described in Example 1.

EXAMPLE 6

Synthesis of 7β-[2-(2-aminothiazol-4-yl)-2(Z)-(hydroxyimino)acetamido]-3-vinyl-3-cephem-4-carboxylic acid 15.0 g (15.2 mmol) of 7β-[2-(2-aminothiazol-4-yl)-2(Z)-(trityloxyimino)acetamido]-3-vinyl-3-cephem-4-carboxylic acid•p-toluenesulfonic acid•2 N,N-dimethylacetamide was dissolved in 9 ml of methanol and then 0.51 ml (15.2 mmol) of 99% formic acid was added thereto. After the resulting mixture was stirred for 5 hours under reflux, the methanol contained therein was removed under reduced pressure and 50 ml of water, 30 ml of tetrahydrofuran and 60 ml of ethylacetate were added to the residue. The pH of the solution was adjusted to 6.5 to 7.5 by adding sodium hydrogen carbonate little by little. The aqueous layer was separated, washed with a solvent mixture of 30 ml of tetrahydrofuran and 60 ml of ethylacetate, and then adjusted to pH 2.4 to 2.8 using 2N-HCl. The crystal thus precipitated was stirred for 1 hour under ice-bath, filtered, washed with 30 ml of water and dried to obtain 5.5 g (Yield 92%) of the title compound as a pale yellow solid.

HPLC Purity: 99.2%;

IR(KBr, cm$^{-1}$): 3300, 1780, 1665, 1180, 1130;

$^1$H-NMR(DMSO-$d_6$) δ: 3.5, 3.80(2H,ABq,J=18 Hz), 5.2 (1H,d,J=5 Hz), 5.3; (1H,d,J=10 Hz), 5.6(1H,d,J=17 Hz), 5.8(1H,dd,J=8 Hz,5 Hz), 6.7(1H,s), 6.9(1H,dd,J=17 Hz,10 Hz), 7.1(2H,brs), 9.4(1H,d,J=8 Hz), 11.3 (1H,brs).

EXAMPLE 7

10.0 g (10.2 mmol) of 7β-[2-(2-aminothiazol-4-yl)-2(Z)-(trityloxyimino)acetamido]-3-vinyl-3-cephem-4-carboxylic acid•p-toluenesulfonic acid•2 N,N-dimethylacetamide was dissolved in 20 ml of methanol and then 20 ml (0.26 mol) of trifluoroacetic acid and 10 ml (92 mmol) of anisole were added thereto. After the mixture was stirred for 5 hours at 40 to 45° C., the methanol contained therein was removed under reduced pressure. The residue was dispersed in 200 ml of ethylacetate, and then the resulting solution was stirred for 30 minutes and filtered. The pale yellow solid thus obtained was dried and dissolved in 60 ml of water, 30 ml of tetrahydrofuran and 60 ml of ethylacetate. The pH of the solution was adjusted to 5.5 to 6.5 by adding sodium hydrogen carbonate little by little. The aqueous layer was separated, washed with a solvent mixture of 30 ml of tetrahydrofuran and 60 ml of ethylacetate, and then adjusted to pH 2.4 to 2.8 using 2N-HCl. The crystal thus precipitated was stirred for 1 hour under ice-bath, filtered, washed with 30 ml of water and dried to obtain 3.6 g (Yield 90%) of 7β-[2-(2-aminothiazol-4-yl)-2(Z)-(hydroxyimino) acetamido]-3-vinyl-3-cephem-4-carboxylic acid as a pale yellow solid. The purity of the product determined by HPLC analysis was 99.4%, and IR and $^1$H-NMR data were identical to those described in Example 6.

EXAMPLE 8

To 5.0 g (5.1 mmol) of 7β-[2-(2-aminothiazol-4-yl)-2(Z)-(trityloxyimino)acetamido]-3-vinyl-3-cephem-4-carboxylic acid•p-toluenesulfonic acid•2 N,N-dimethylacetamide was added 15 ml of 85% formic acid and the mixture was stirred for 2 hours at room temperature. After tritylcarbinol thus precipitated was removed by filtration, the filtrate was concentrated under reduced pressure. To the residue were added 30 ml of water, 10 ml of tetrahydrofuran and 20 ml of ethylacetate. The pH of the solution was adjusted to 6.5 by adding sodium hydrogen carbonate little by little. The aqueous layer was separated, washed with a solvent mixture of 10 ml of tetrahydrofuran and 20 ml of ethylacetate, and then adjusted to pH 2.4 to 2.8 using 2N-HCl. The crystal thus precipitated was stirred for 1 hour under ice-bath, filtered, washed with 10 ml of water and dried to obtain 1.9 g (Yield 93%) of 7β-[2-(2-aminothiazol-4-yl)-2(Z)-(hydroxyimino) acetamido]-3-vinyl-3-cephem-4-carboxylic acid as a pale yellow solid. The purity of the product determined by HPLC analysis was 99.1%, and IR and $^1$H-NMR data were identical to those described in Example 6.

What is claimed is:

1. A process for preparing cefdinir having the following formula (I),

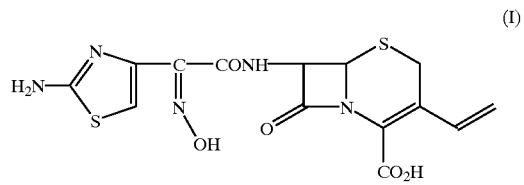

characterized in that a trityl protecting group in a cefdinir intermediate having the following formula (II),

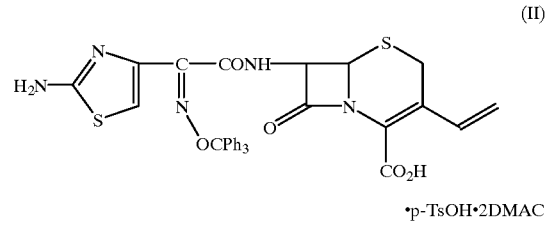

in which Ph represents phenyl, p-TsOH represents p-toluenesulfonic acid, and DMAC represents, N,N-dimethylacetamide, is removed by reacting with an inorganic acid, an organic acid, or an acidic hydrogen ion exchange resin.

2. A process for preparing a compound having the following formula (II),

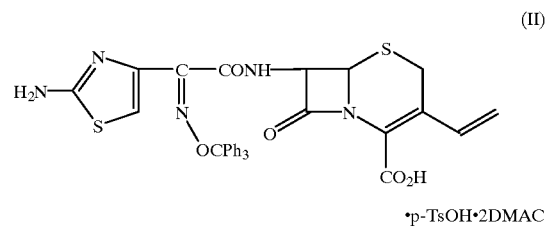

in which Ph represents phenyl, p-TsOH represents p-toluenesulfonic acid, and DMAC represents N,N-dimethylacetamide, characterized in that a reactive ester having the following formula (III),

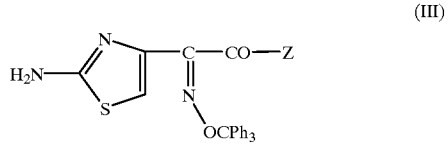

in which Z represents

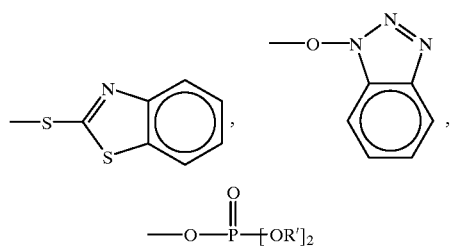,

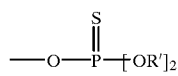

or

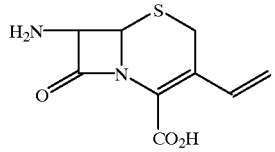

wherein R' represents $C_1$–$C_4$ alkyl or phenyl, which is reacted with a 3-cephem derivative having the following formula (IV), (IV)

in a solvent comprising DMAC in the presence or absence of a base, and then p-toluenesulfonic acid is added thereto.

3. The process according to claim 1, wherein the inorganic acid is selected from a group consisting of hydrochloric acid, hydrobromic acid, hydroiodic acid, sulfuric acid and Lewis acid.

4. The process according to claim 3, wherein the Lewis acid is selected from a group consisting of boron trifluoride, boron trifluoride ethyletherate, aluminum chloride, antimony pentachloride, ferrous chloride, stannous chloride, titanium tetrachloride and zinc chloride.

5. The process according to claim 1, wherein the organic acid is selected from a group consisting of acetic acid, formic acid, trifluoroacetic acid, methanesulfonic acid, benzenesulfonic acid and p-toluenesulfonic acid.

6. The process according to claim 1, wherein the reaction is carried out in the presence of a cation scavenger when a Lewis acid or an organic acid is used.

7. The process according to claim 6, wherein the cation capturing agent is anisole.

8. The process according to claim 1, wherein the acid is used in an amount of 1 to 20 equivalents with respect to the compound of formula (II).

9. A crystalline cefdinir intermediate having the following formula (II):

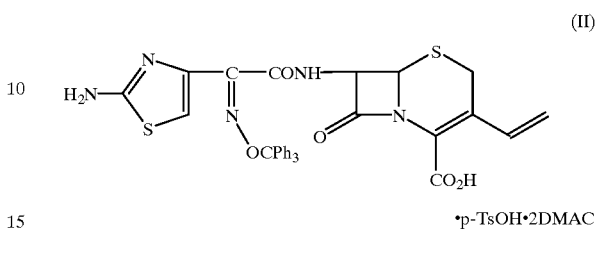

·p-TsOH·2DMAC in which

Ph represents phenyl, p-TsOH represents p-toluenesulfonic acid, and

DMAC represents N,N-dimethylacetamide.

10. The process according to claim 2, wherein diethylether, diisopropylether or ethylacetate is added in an amount of 2 to 6 times by volume with respect to the reaction solvent as an additional work-up procedure.

11. The process according to claim 2, wherein p-toluenesulfonic acid is used in an amount of 1 to 3 equivalents with respect to the 3-cephem derivative of formula (IV).

12. The process according to claim 2, wherein the reactive ester of formula (III) is used in an amount of 0.8 to 2.0 equivalents with respect to the 3-cephem derivative of formula (IV).

13. The process according to claim 2, wherein the solvent is N,N-dimethylacetamide alone, or a mixture of N,N-dimethylacetamide with one or more selected from a group consisting of ethanol, methanol, isopropanol, diethylether, tetrahydrofuran, dioxane, methylene chloride, chloroform, acetonitrile, ethylacetate and acetone.

14. The process according to claim 2, wherein the reaction is carried out at a temperature of −15 to 40° C.

15. The process according to claim 2, wherein a tertiary amine is used as the base.

16. The process according to claim 15, wherein the tertiary amine is triethylamine or tri-n-butylamine.

17. The process according to claim 2, wherein N-trimethylsilylacetamide or N,O-bistrimethylsilylacetamide is used in the absence of a base.

* * * * *